United States Patent [19]

Mendiratta et al.

[11] Patent Number: 4,546,207
[45] Date of Patent: Oct. 8, 1985

[54] PROCESS FOR PREPARING ANHYDROUS SALTS OF DIHYDROXYAROMATIC COMPOUNDS

[75] Inventors: Ashok K. Mendiratta, Schenectady, N.Y.; Subhas K. Sikdar, Boulder, Colo.

[73] Assignee: General Electric Company, Schenectady, N.Y.

[21] Appl. No.: 633,740

[22] Filed: Jul. 23, 1984

Related U.S. Application Data

[63] Continuation-in-part of Ser. No. 470,856, Feb. 28, 1983, abandoned.

[51] Int. Cl.$^4$ .............................................. C07C 37/68
[52] U.S. Cl. ................................... 568/723; 568/716; 568/722; 568/753; 568/763
[58] Field of Search ............... 568/722, 723, 724, 753, 568/763, 716

[56] References Cited

U.S. PATENT DOCUMENTS

| | | | |
|---|---|---|---|
| 2,354,012 | 7/1944 | Gump | 568/722 |
| 3,960,968 | 6/1976 | Vernaleken et al. | 568/723 |
| 4,202,993 | 5/1980 | Takekoshi | 568/723 |
| 4,221,673 | 9/1980 | Robson et al. | 568/723 |
| 4,257,953 | 3/1981 | Williams, III et al. | 568/722 |
| 4,302,616 | 11/1981 | Williams, III et al. | 568/722 |
| 4,410,735 | 10/1983 | Dellacoletta et al. | 568/722 |
| 4,467,123 | 8/1984 | Mayer et al. | 568/722 |

Primary Examiner—Werren B. Lone
Attorney, Agent, or Firm—William H. Pittman; James C. Davis, Jr.; James Magee, Jr.

[57] ABSTRACT

Anhydrous di-(alkali metal) (especially disodium) salts of dihydroxyaromatic compounds such as bisphenol A are prepared by first contacting the solid dihydroxyaromatic compound with an aqueous alkali metal hydroxide solution so as to convert it into the solid di-(alkali metal) salt or hydrate thereof and subsequently separating the solid salt or hydrate from the aqueous system and removing water therefrom, typically by mixing the same with an organic liquid and removing water, including water of hydration, by evaporation. The organic liquid is preferably one such as toluene or o-dichlorobenzene in which water and the anhydrous di-(alkali metal) salt are substantially insoluble. The process may be operated in batch or continuous fashion.

14 Claims, 4 Drawing Figures

FIG. I
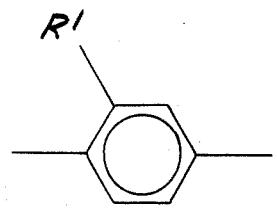
FIG. II
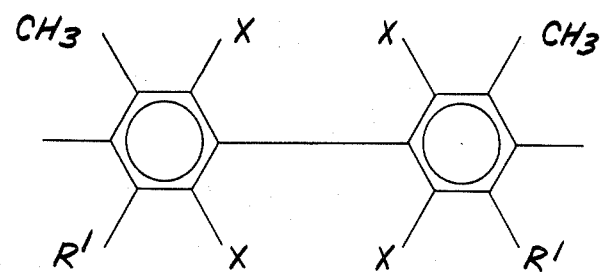
FIG. III
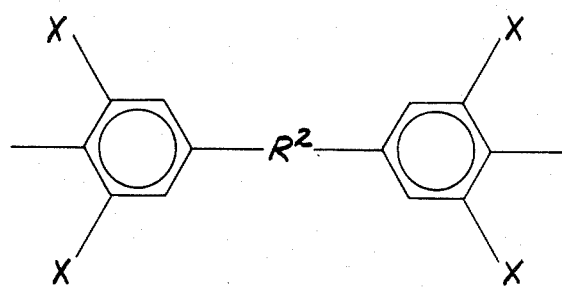

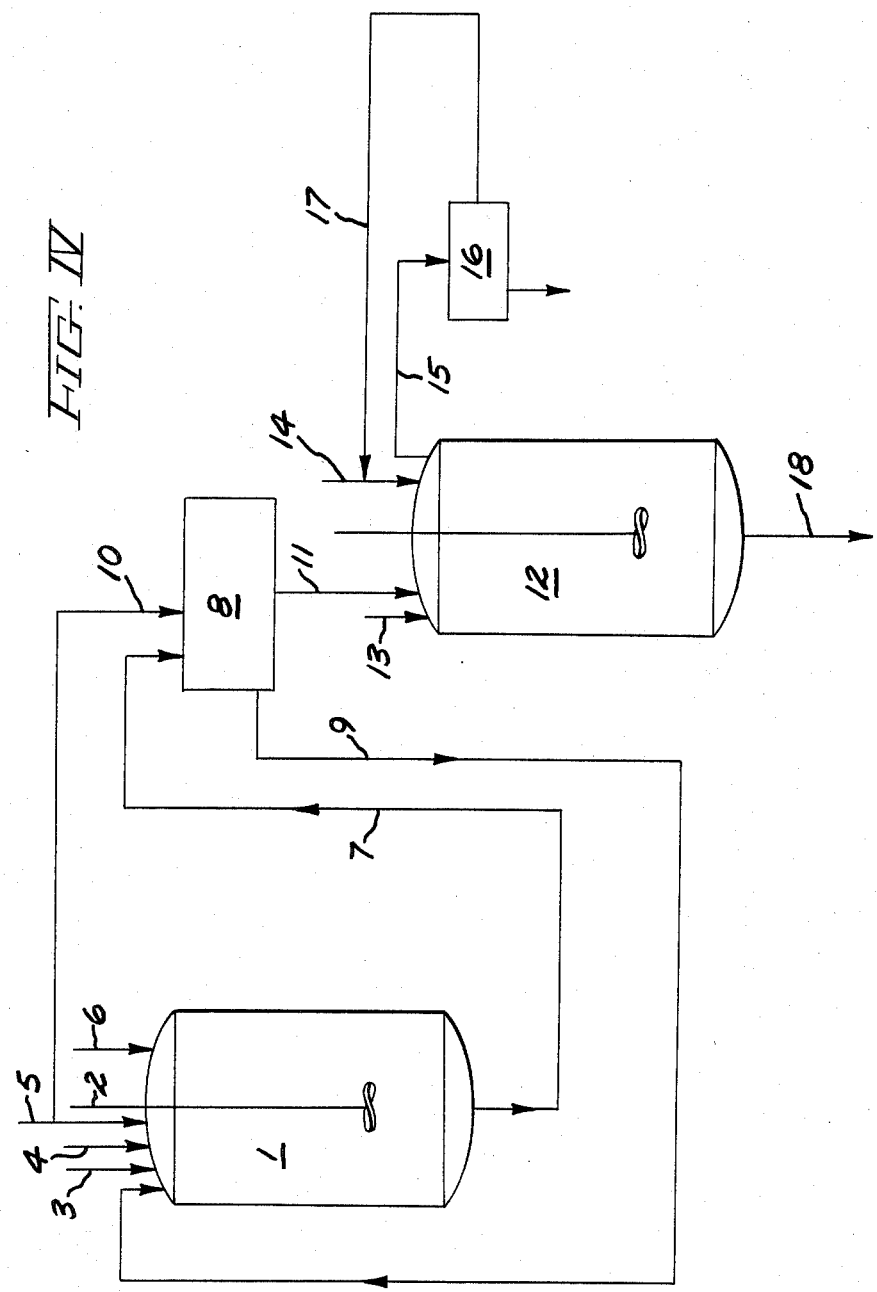
FIG. IV

PROCESS FOR PREPARING ANHYDROUS SALTS OF DIHYDROXYAROMATIC COMPOUNDS

This application is a continuation-in-part of copending application Ser. No. 470,856, filed Feb. 28, 1983, now abandoned.

This invention relates to the preparation of di-(alkali metal) salts of dihydroxyaromatic compounds and to a method of recovery thereof.

The preparation of di-(alkali metal) salts of dihydroxyaromatic compounds typically and conveniently takes place in an aqueous system. Many commercially important reactions of said salts, however, such as their reaction with nitrophthalimides to form aromatic ether imides, are best carried out under anhydrous conditions to maximize yields. It is necessary, therefore, to isolate the salt in anhydrous form.

Various methods for removal of water from such salts have been disclosed. For example, U.S. Pat. No. 4,202,993 describes a flash evaporation method, while U.S. Pat. No. 4,257,953 discloses azeotropic distillation of the water using a hydrocarbon solvent such as toluene. While these methods are effective, they suffer from certain disadvantages. For example, the presence of alkali metal hydroxide may be detrimental in subsequent reactions, such as the reaction with nitrophthalimide. Since no measures are taken in these methods to remove alkali metal hydroxide, it is necessary to carefully monitor and maintain at stoichiometric the proportion thereof used for converting the dihydroxyaromatic compound to its di-(alkali metal) salt. Also, a large amount of toluene is required to insure the azeotropic removal of the relatively large quantity of water (often about 2-3 parts by weight per part of dihydroxyaromatic compound) used in the reaction, and the di-(alkali metal) salt is susceptible to caking during the removal of water.

A principal object of the present invention, therefore, is to provide an improved process for the preparation of di-(alkali metal) salts of dihydroxyaromatic compounds.

A further object is to provide an improved method for the removal of water from such salts.

A further object is to provide a metal for recovery of such salts in anhydrous form as free-flowing solids, adapted for easy handling during further reactions.

Still another object is to provide a method for the preparation of such salts which is flexible, involves a minimum of operations and reaction monitoring steps, and is adaptable to continuous operation.

A still further object is to prepare such salts by a method involving a minimum of energy expenditure for heating and the like.

Other objects will in part be obvious and will in part appear hereinafter.

In its broadest sense, the present invention is directed to a process for recovering in anhydrous form a di-(alkali metal) salt of a dihydroxyaromatic compound which comprises:

(A) contacting solid dihydroxyaromatic compound with an aqueous solution of an alkali metal hydroxide for a period of time sufficient to convert said compound to its solid di-(alkali metal) salt or a hydrate thereof;

(B) separating said salt or its hydrate from the aqueous system; and (C) removing water, including water of hydration, from said salt or hydrate.

The dihydroxyaromatic compounds which may be converted to alkali metal salts according to the process of this invention generally have the formula HO—Z—OH, wherein Z has one of the formulas in FIGS. I, II and III of the drawings. In these formulas, each $R^1$ is independently hydrogen or methyl, $R^2$ is a straight-chain or branched alkylene radical containing 1-5 carbon atoms and is most often the isopropylidene radical, and each X is independently hydrogen or halogen (usually chlorine or bromine). The compounds in which Z has formula III are disphenols. Since the invention is particularly useful for the preparation of bisphenol salts, frequent reference to bisphenols will be made hereinafter. However, the invention can also be used to prepare salts of compounds in which Z has formula I or II, or of mixtures of compounds in which Z has any or all of these formulas. The preferred bisphenol is bisphenol A, i.e., 2,2-bis(4-hydroxyphenyl)propane, which has the formula in FIG. III wherein $R^2$ is isopropylidene and each X is hydrogen.

The di-(alkali metal) salts which are formed by the process of this invention are those of the metals of Group IA of the Periodic Table; namely, lithium, sodium, potassium, rubidium and cesium. For reasons of economy and availability, the sodium and potassium salts, especially the former, are preferred. Therefore, reference hereinafter will frequently be made to sodium as the alkali metal used. It should be understood, however, that other alkali metals can be substituted for sodium.

In step A of the process of this invention, the solid bisphenol is contacted with an aqueous sodium hydroxide solution. This solution typically comprises about 10–50% by weight, preferably about 10–30%, sodium hydroxide. The weight ratio of water to bisphenol during this step is usually from about 2:1 to about 3:1.

Contact during step A is typically effected at a temperature below about 75° and especially below about 45° C., preferably within the range of about 10°–50° and most desirably about 25°–50° C. At temperatures within this range, the bisphenol is substantially insoluble in the aqueous system. Nevertheless, it undergoes a heterogeneous reaction with the sodium hydroxide to yield the desired disodium salt, which in the case of bisphenol A separates as the solid hydrate which is also substantially insoluble at these temperatures. However, the process of this invention is not limited to salts which form hydrates; it may also be used to prepare other salts which are substantially insoluble under the conditions described.

It is ordinarily desirable to achieve substantially complete conversion of the bisphenol to its sodium salt. Therefore, at least a stoichiometric amount of sodium hydroxide (i.e., at least one equivalent per equivalent of bisphenol) should be used. In order to insure completeness of the reaction, it is frequently advantageous to use up to about 20% excess sodium hydroxide, most often up to about 10%. One of the advantages of this invention is that excess sodium hydroxide may be used without adversely affecting the product.

The residence time required for completion of step A is normally about 2-4 hours. The reaction will, of course, be faster at higher temperatures within the preferred range, but hydrate recovery may be lower because of increased salt or hydrate solubility in water at higher temperatures. Optimum conditions are frequently attained at 25°–40° C. and a residence time of about 3-4 hours.

Step B comprises separation of the solid salt or hydrate from the aqueous system. Separation is typically accomplished by known processes such as filtration or centrifugation.

In step C, water (including any water of hydration) is removed from the solid salt or hydrate obtained in step B. This is usually conveniently accomplished by mixing the same with an organic liquid to create a system adapted for water removal by evaporation. A wide variety of organic liquids can be used; in general, they comprise all liquids which have a boiling point higher than that of water (i.e., higher than 100° C.) or which form azeotropes with water. These conditions are applicable because a liquid which has a lower boiling point than water and does not form an azeotrope therewith will itself be removed by evaporation before the water is removed.

Typical organic liquids which may be used in step C include benzene, toluene, xylene, chlorobenzene, o-dichlorobenzene, heptane, octane, nonane, decane, petroleum naphthas with a higher boiling point than that of water, chloroform, carbon tetrachloride, ethylene glycol, ethylene glycol monoethyl ether, diethylene glycol, diethylene glycol dimethyl ether, diethylene glycol dibutyl ether, 2-butanol, dioxane and methyl isobutyl ketone. While the degree of solubility of water in the organic liquid is not critical, it is preferred to use liquids in which water is substantially insoluble and which boil above 105° C. and preferably below about 200° C., and especially those in which the bisphenol sodium salt is substantially insoluble. The aromatic hydrocarbons and chlorinated hydrocarbons (e.g., benzene, toluene, xylene, chlorobenzene, o-dichlorobenzene) are especially suitable; of these, toluene and o-chlorobenzene are most desirable because of their effectiveness, availability and relatively low price.

The weight ratio of organic liquid to salt or hydrate used in step C depends to some extent on the creation or non-creation of an azeotropic mixture, the proportions of the liquids in that mixture, and the creation of a free-flowing slurry of the salt hydrate. Generally, about 1–3 parts by weight of organic liquid per part of salt or hydrate is sufficient. The preferred ratio is between about 1.5:1 and about 2:1.

Evaporative drying and/or dehydration of the solid salt or hydrate may be effected by flash evaporation, distillation or the like. Often, a portion of the organic liquid is simultaneously removed by evaporation, especially when it forms an azeotrope with water, but evaporation of the organic liquid is not an essential step of the process. When a water-immiscible liquid such as toluene is used, it is frequently convenient to introduce said liquid at an elevated temperature, typically about 100° C., continuously or intermittently until the condensate no longer contains a substantial amount of water. Typically, drying is complete when said condensate contains less than about 100 ppm. and preferably less than about 50 ppm. of water.

Following step C, the dry anhydrous disodium salt may be separated from the organic liquid. The method of separation will vary according to whether the salt is soluble or insoluble in the organic liquid. If it is soluble, the liquid may typically be removed by evaporation at atmospheric or reduced pressure. In the preferred embodiment which employs a liquid in which the anhydrous disodium salt is substantially insoluble, separation is relatively simple and may be effected by filtration, centrifugation or the like. Remaining traces of organic liquid in the salt may be removed by vacuum drying or a similar operation. It is, however, often most convenient to employ the salt in slurry form. An illustration is its reaction with a nitrophthalimide. For such uses, separation of the salt from the organic liquid is unnecessary.

The process of this invention has many advantages over previously known processes involving such expedients as azeotropic removal of all the water in which the sodium salt was dissolved. In the first place, as previously mentioned, it is possible to employ an excess of sodium hydroxide in the formation of the disodium salt of the bisphenol. This fact, combined with the rapidity of water removal, substantially decreases the time required for salt preparation. In the second place, according to the process of this invention as much as 70% by weight of the total water in the system is removed relatively simple in step B, with a relatively small amount remaining for removal in step C; therefore, energy usage for vaporization in step C is minimized. In the third place, the anhydrous bisphenol disodium salt is obtained as a free-flowing solid with little or no tendency to agglomerate or cake. In the fourth place, the process can be adapted for continuous operation.

Reference is now made to FIG. IV of the drawings which depicts a typical reaction system for the practice of the process of this invention. Reactor 1 is a tank-type reactor fitted with stirring means 2 and also with temperature control means (not shown), and typically also contains baffles (not shown) to insure thorough agitation of the contents. Aqueous sodium hydroxide, bisphenol and water are introduced into reactor 1 through feeders 3, 4 and 5 respectively; bisphenol feed 4 is a solids feeder such as a screw conveyor. An inert atmosphere is typically maintained in reactor 1 by the addition of an inert gas such as nitrogen at 6. The mixture in reactor 1 is agitated for a period of time sufficient to convert substantially all the bisphenol to its disodium salt; the aqueous slurry of the salt hydrate is pumped through line 7 into separation means 8, typically a filter or centrifuge. The mother liquor is recycled through line 9 to reactor 1. If necessary, water may be added via line 10 to wash the hydrate crystals. If this is done, such water is normally part of the feed water introduced at 5 to avoid dilution of the sodium hydroxide solution in reactor 1.

The solid hydrate from separation means 8 passes through line 11 into stirred separation vessel 12, which is also typically maintained in an inert gas at 13. The organic liquid, typically toluene or o-dichlorobenzene, is introduced at 14 and the mixture is stirred and heated by temperature control means (not shown). Water and organic liquid are removed by evaporation at 15 and separated by liquid-liquid separation means 16, the organic liquid being returned via line 17 to separation vessel 12. When water removal is substantially complete and the slurry of anhydrous bisphenol disodium salt in the organic liquid is drained through line 18. It may be used in slurry form or separated by conventional means from the organic liquid, which may then be recycled.

The process of this invention may be performed in batch or continuous fashion. When continuous operation is employed, it is sometimes advantageous to interpose a holding vessel (not shown) between reactor 1 and separation means 8 in FIG. IV, proceeding therefrom in either batch or continuous fashion in the separation and subsequent stages. It is also sometimes found that the product effluent of the continuous process from separation means 8 contains an undesirably high alkali metal hydroxide content. If so, said product may be washed with additional water as described hereinabove (typically above 1 part by weight per 2.8–3.5 parts of reactant bisphenol) after step B to remove said hydroxide.

The invention is illustrated by the following examples. All parts and percentages are by weight.

EXAMPLE 1

A mixture of 700 parts (3.07 moles) of solid bisphenol A, 590 parts of 50% aqueous sodium hydroxide solution (7.38 moles of sodium hydroxide or a 20% excess) and 1400 parts of water was prepared in a reactor equipped with vertical baffles and a pitched blade turbine impeller. The reaction between the sodium hydroxide and bisphenol A was conducted for 2.5 hours at 35° C. The contents of the reactor were centrifuged and 950 parts of wet solids were recovered; analysis of the solids showed that only negligible amounts of bisphenol A, sodium hydroxide and the monosodium salt were present therein. The solid cake was returned to the reactor and 1950 parts of toluene were added. The contents of the reactor were evaporated, with periodic addition of hot toluene to maintain the liquid level. When the liquid removed by evaporation contained less than 50 ppm. of water, the toluene-salt slurry was removed. The bisphenol A disodium salt therein was in finely divided, free-flowing form with no lumps or cakes.

EXAMPLE 2

The procedure of Example 1 was repeated, substituting o-dichlorobenzene on a weight basis for toluene. The results were similar, except that water removal was faster and required less organic liquid owing to the higher boiling point of o-dichlorobenzene.

EXAMPLE 3

The reactor was similar to that used in Example 1 except that it contained an overflow exit near the top. It was charged with a feed mixture consisting of 26% bisphenol A, 11% sodium hydroxide (provided as a 50% aqueous solution) and 63% water (total). The total volume of the mixture was 3.10 liters. The mixture was stirred for 2 hours at 40°–45° C., after which the following were added continuously over 8 hours at the recited rates:

Bisphenol A—5.5 grams per minute (by means of a screw conveyor).

15% aqueous sodium hydroxide solution—15.7 grams per minute.

These amounts preserved an excess sodium hydroxide concentration of 21%, a weight ratio of water to bisphenol A of 2.43 and a residence time of about 3 hours.

After steady-state conditions had been attained, operation of the system in this fashion was continued for 8 hours, during which time the reactor effluent was collected in a holding vessel. Water was removed from a 908-gram sample of the effluent by means of a basket centrifuge. The solids were then washed with 75 grams of water to remove sodium hydroxide and the solid product (260 grams) was dried azeotropically with toluene. The bisphenol A disodium salt was recovered in high purity in finely divided, free-flowing form.

What is claimed is:

1. A process for recovering an alkali metal salt of a dihydroxyaromatic compound having the formula HO—Z—OH, wherein Z has the formula

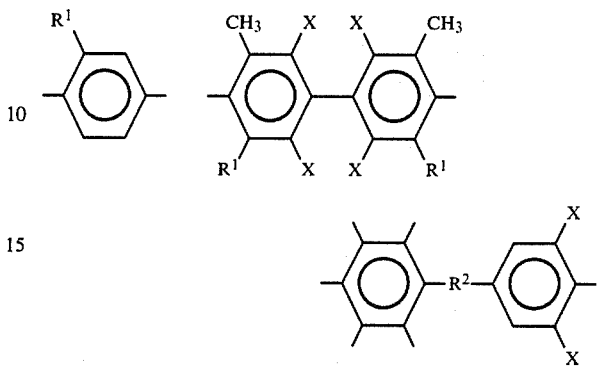

each $R^1$ is independently hydrogen or methyl, $R^2$ is a straight-chain or branched alkylene radical containing 1–5 carbon atoms and each X is independently hydrogen or halogen, which comprises:

(A) forming an aqueous slurry by contacting solid dihydroxyaromatic compound with an aqueous solution of an alkali metal hydroxide for a period of time sufficient to convert said compound to its solid di-(alkali metal) salt, or a hydrate thereof;

(B) separating said salt or its hydrate from the aqueous system; and (C) removing water, including water of hydration, from said salt or hydrate.

2. A process according to claim 1 wherein the alkali metal is sodium.

3. A process according to claim 1 wherein step A is effected at a temperature below about 45° C.

4. A process according to claim 3 wherein step C is effected by mixing said salt or hydrate with an organic liquid to create a system adapted for removal of water and removing said water by evaporation.

5. A process according to claim 4 wherein the dihydroxyaromatic compound is bisphenol A.

6. A process according to claim 4 wherein the organic liquid is one in which water and the anhydrous disodium salt are substantially insoluble.

7. A process according to claim 6 wherein the organic liquid boils above 105° C.

8. A process according to claim 7 wherein the organic liquid is toluene or o-dichlorobenzene.

9. A process according to claim 8 wherein an excess of sodium hydroxide up to about 20% is used in step A.

10. A process according to claim 9 wherein the organic liquid is toluene.

11. A process according to claim 10 wherein the organic liquid is o-dichlorobenzene.

12. A process according to claim 1, 4 or 8 which is performed in continuous fashion.

13. A process according to claims 12 wherein alkali metal hydroxide is removed from the product after step B by washing with water.

14. A process according to claim 13 wherein the amount of water used to remove said alkali metal hydroxide is about 1 part by weight per 2.8–3.5 parts of reactant dihydroxyaromatic compound.

* * * * *